(12) United States Patent
Petela et al.

(10) Patent No.: US 10,022,699 B2
(45) Date of Patent: Jul. 17, 2018

(54) FURNACE COIL FINS (71) Applicant: NOVA Chemicals (International) S.A., Fribourg (CH)

(72) Inventors: Grazyna Petela, Calgary (CA); Leslie Wilfred Benum, Red Deer (CA); Edward Christopher Foy, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 15/891,407

(22) Filed: Feb. 8, 2018

(65) Prior Publication Data

US 2018/0161751 A1    Jun. 14, 2018

Related U.S. Application Data

(60) Continuation of application No. 14/819,917, filed on Aug. 6, 2015, which is a division of application No. (Continued)

(30) Foreign Application Priority Data

Mar. 31, 2011   (CA) .................................... 2735533
Jun. 29, 2011   (CA) .................................... 2746285

(51) Int. Cl.
*B01J 19/00*       (2006.01)
*F28F 1/14*        (2006.01)
(Continued)

(52) U.S. Cl.
CPC ........... *B01J 19/2415* (2013.01); *B01J 19/00* (2013.01); *B01J 19/006* (2013.01); *B01J 19/0013* (2013.01); *B01J 19/02* (2013.01); *C07C 4/04* (2013.01); *C10G 9/20* (2013.01); *C10G 9/203* (2013.01); *F28F 1/14* (2013.01); *F28F 1/24* (2013.01); *F28F 21/083* (2013.01); *B01J 2219/00076* (2013.01); *B01J 2219/00157* (2013.01); *B01J 2219/0286* (2013.01);
(Continued)

(58) Field of Classification Search
CPC ................................... B01J 19/00; F28F 1/14
USPC ......................................................... 422/198
See application file for complete search history.

(56) References Cited

U.S. PATENT DOCUMENTS 3,205,048 A * 9/1965 Diessel .................... C07C 4/04
                                                      196/110
5,590,711 A    1/1997 Ishida et al.
(Continued)

OTHER PUBLICATIONS

Siddique et al., Recent Advances in Heat Transfer Enhancements, J. Chem. Eng., vol. 2010, 2010, Article ID 106461, pp. 1-28.
(Continued)

*Primary Examiner* — Huy Tram Nguyen
(74) *Attorney, Agent, or Firm* — Julie L. Heinrich (57) ABSTRACT

The present invention provides low profile, thick ("stubby") longitudinal fins having a cross section which is a parallelogram, trapezoid or a triangle extending from 10% to 100% of a coil pass and comprising from 3 to 45 weight % of a coil in a radiant section of a furnace for thermally cracking one or more of paraffins and naphtha. The fins provide an additional surface through which heat may be transferred to the coil making the coil more efficient reducing greenhouse emissions.

20 Claims, 10 Drawing Sheets

Related U.S. Application Data

13/406,703, filed on Feb. 28, 2012, now Pat. No. 9,132,409.

(51) Int. Cl.
| | |
|---|---|
| *B01J 19/24* | (2006.01) |
| *C07C 4/04* | (2006.01) |
| *F28F 1/24* | (2006.01) |
| *F28F 21/08* | (2006.01) |
| *C10G 9/20* | (2006.01) |
| *B01J 19/02* | (2006.01) |
| *F28D 21/00* | (2006.01) |

(52) U.S. Cl.
CPC ... *B01J 2219/24* (2013.01); *C10G 2300/1044* (2013.01); *C10G 2300/1081* (2013.01); *C10G 2300/4043* (2013.01); *F28D 2021/0022* (2013.01)

(56) References Cited

U.S. PATENT DOCUMENTS

| | | |
|---|---|---|
| 5,950,718 A | 9/1999 | Sugitani et al. |
| 7,096,931 B2 * | 8/2006 | Chang .................. B01J 8/1836 165/133 |
| 7,128,139 B2 | 10/2006 | Oballa et al. |
| 7,278,828 B2 | 10/2007 | Steplewski et al. |

OTHER PUBLICATIONS

Detemmerman et al., Three dimensional couples simulation of furnaces and reactor tubes for the thermal cracking of HC's, Rev. IFP, vol. 53, No. 2, Mar.-Apr. 1998, pp. 181-194.

De Saegher et al., Three dimensional simulation of high severity internally finned cracking coils for olefin production, Universiteit Gent., Dec. 1995; pp. 245-260.

\* cited by examiner

FURNACE COIL FINS

FIELD OF THE INVENTION

The present invention relates to the field of cracking paraffins to olefins and more particularly to substantially linear longitudinal vertical fins on the external surface of the vertical portion of process coil(s) in the radiant section of a cracking furnace. More particularly, the fins on the coils may have a parallelogram (square and rectangular), triangular or trapezoidal cross section, relatively flat/thick profile ("stubby") and have a mass less than about 45 weight % of the total weight of the furnace coils. These fins intensify radiant and convective heat transfer to the process coils from flame, combustion gases and furnace walls surrounding the coil.

BACKGROUND OF THE INVENTION

The field of heat exchanger designs is replete with applications of fins to improve the heat transfer, as disclosed in the review "Recent Advances in Heat Transfer Enhancements: A Review Report" by Siddique et al., Int. Journal of Chem. Eng, 28 pages, vol. 2010, (2010).

Typically this is heat transfer by forced convection mechanism. The heat transfer by forced convection takes place between a solid surface and fluid in motion, which may be gas or liquid, and it comprises the combined effects of conduction and fluid flow. This type of heat transfer occurs in most of the conventional heating systems, either hot water or electric and industrial heat exchangers.

In the cracking process of a paraffin such as ethane or naphtha, the feed flows through a furnace coil (pipe) that is heated up to 1050° C., inside the radiant section of a cracking furnace. At these temperatures, the feed undergoes a number of reactions, including a free radical decomposition (cracking), reformation of a new unsaturated product and the coproduction of hydrogen. These reactions occur over a very short period of time that corresponds to the feed residence time in a coil.

The interior of the radiant section of the furnace is lined with heat absorbing/radiating refractory and is heated typically by gas fired burners. The heat transfer within the furnace, between flame, combustion gases, refractory and the process coils is mostly by radiation and also by forced convection.

There is a drive to improve the efficiency of cracking furnaces as this reduces process costs and greenhouse gas emissions. There have been two main approaches to improving efficiency: the first one by improving heat transfer to the furnace coils, i.e. from flame, combustion gases and refractory walls to the external surface of a process coil, and the second one by improving heat transfer within the coil, i.e. from the coil walls into the feed flowing inside the coil.

One of the methods representing the second approach is the addition of internal fins to the inner walls of the furnace coil to promote the "swirling" or mixing of the feed within the coil. This improves the convective heat transfer from the coil walls to the feed as the turbulence of the feed flow is increased and the heat transferring surface of the hot inner wall of the coil is increased as well.

U.S. Pat. No. 5,950,718 issued Sep. 14, 1999 to Sugitani et al. assigned to Kubota Corporation provides one example of this type of technology.

The papers "Three dimensional coupled simulation of furnaces and reactor tubes for the thermal cracking of hydrocarbons", by T. Detemmerman, G. F. Froment, (Universiteit Gent, Krijgslaan 281, b-9000 Gent—Belgium, mars-avri, 1998); and "Three dimensional simulation of high internally finned cracking coils for olefins production severity", by Jjo de Saegher, T. Detemmerman, G. F. Froment, (Universiteit Gent1, Laboratorium voor Petrochernische Techniek, Krijgslaan 281, b-9000 Gent, Belgium, 1998) provide a theoretical simulation of a cracking process in a coil which is internally finned with helicoidal and longitudinal fins (or rather ridges or bumps). The simulation results are verified by lab scale experiments, where hot air flows through such internally finned tubes. The papers conclude that the tube with internal helicoidal fins performs better than with internal longitudinal fins and that the results for "a tube with internal helicoidal fins are in excellent agreement with industrial observations". However, no experimental data are provided to support these conclusions. There is also no comparison made to the performance of a bare tube, with no internal ribs or fins. The authors agree that one potential disadvantage of such coils with internal fins is that carbon deposits may build up on the fins, increasing the pressure drop through the tube.

U.S. Pat. No. 5,590,711 issued Jan. 7, 1997 to Ishida et al. assigned to Kabushiki Kasha Kobe Seiko Sho, discloses heat exchanger tubes having a plurality of external crests and ridges on their surface. The tubes are used in refrigeration and air conditioning applications, in which a liquid (e.g. water) is in direct contact with the external surface of the tube. The patent does not suggest the tubes could be used in a radiant section of a cracking furnace. Further the patent does not teach fins but rather teaches "groves".

U.S. Pat. No. 7,096,931 issued Aug. 29, 2006 to Chang et al. assigned to ExxonMobil Research and Engineering Company teaches an externally finned heat exchanger tube in a slurry reaction (Fischer Tropsch synthesis). In the reaction, a slurry of CO and hydrogen in a hydrocarbyl diluent containing catalyst flows over heat exchanger tubes containing flowing cooling water. The water is heated to steam in the process, to remove the heat of reaction.

Both of the preceding patents teach heat exchange by forced convection. That is a flowing fluid (water or a hydrocarbon) is in contact with the external surface of a heating/cooling tube which has groves or fins on its surface. Neither of the patents suggests external fins to enhance the radiative heat transfer to the tube.

NOVA Chemicals U.S. Pat. No. 7,128,139 issued Oct. 31, 2006 teaches external annular fins on the cracking furnace coil to increase convection heat exchange to the coil. The reference teaches away from the subject matter of the present invention as the fins are not longitudinal vertical (claims 15 and 16).

The present invention seeks to provide a method to increase the radiant and convective heat capture by a process coil in the radiant heating section of a cracking furnace.

SUMMARY OF THE INVENTION

The present invention provides an improvement in a furnace for thermally cracking a feed selected from the group consisting of $C_{2-4}$ alkanes, and naphtha, the improvement comprising using in the furnace radiant section one or more process coils comprising one or more passes, having from 1 to 8 substantially linear longitudinal vertical fins on its external surface, said fins having:
  i) a length from 10 to 100% of the length of the coil pass;
  ii) a cross section that is selected from the group consisting of a parallelogram, a triangle, and a trapezoid, iii) a base having a width from 3% to 30% of the coil outer diameter, which base has continuous contact with, or is integrally part of the coil pass;
iv) a height from 10% to 50% of the coil outer diameter, and
v) a weight from 3% to 45% of the total weight of the coil pass.

In a further embodiment the number of fins is from one to four.

In a further embodiment the fin has a base with a width from 4%-20% of the coil outer diameter.

In a further embodiment the fin has a height from 13%-35% of the coil outer diameter.

In a further embodiment, there are two said fins on the furnace coil, radially spaced from 160° to 200° from each other about the external surface of the furnace coil.

In a further embodiment the cross section of the fin is a parallelogram.

In a further embodiment the cross section of the fin is triangular.

In a further embodiment the cross section of the fin is trapezoidal.

In a further embodiment only the selected passes of the furnace coil in the radiant section have fins. In a further embodiment the furnace radiant coil comprises from about 55 to 65 weight % of Ni; from about 20 to 10 weight % of Cr; from about 20 to 10 weight % of Co; and from about 5 to 9 weight % of Fe and the balance one or more of the trace elements.

In a further embodiment wherein the trace elements in the above coil comprise from 0.2 up to 3 weight % of Mn; from 0.3 to 2 weight % of Si; less than 5 weight % of titanium, niobium and all other trace metals; and carbon in an amount of less than 0.75 weight % the sum of the components adding up to 100 weight %.

In a further embodiment the alloy may contain up to 3 weight % of aluminum.

In a further embodiment the furnace radiant coil comprises from 40 to 65 weight % of Co; from 15 to 20 weight % of Cr; from 20 to 13 weight % of Ni; less than 4 weight % of Fe and the balance of one or more trace elements and up to 20 weight % of W the sum of the components adding up to 100 weight %.

In a further embodiment the trace elements in the above coil comprise from 0.2 up to 3 weight % of Mn; from 0.3 to 2 weight % of Si; less than 5 weight % of titanium, niobium and all other trace metals; and carbon in an amount of less than 0.75 weight %

In a further embodiment the alloy may contain up to 3 weight % of aluminum.

In a further embodiment the furnace radiant coil comprises from 20 to 38 weight % of chromium from 25 to 48, weight % of Ni.

In a further embodiment the above radiant coil further comprises from 0.2 up to 3 weight % of Mn, from 0.3 to 2 weight % of Si; less than 5 weight % of titanium, niobium and all other trace metals; and carbon in an amount of less than 0.75 weight % and the balance substantially iron.

In a further embodiment the alloy may contain up to 7 weight % of aluminum.

DETAILED DESCRIPTION

As used in this specification radially spaced means the spacing of the vertical fins, in degrees, about the circumference of the pipe or pass.

Figure 1:
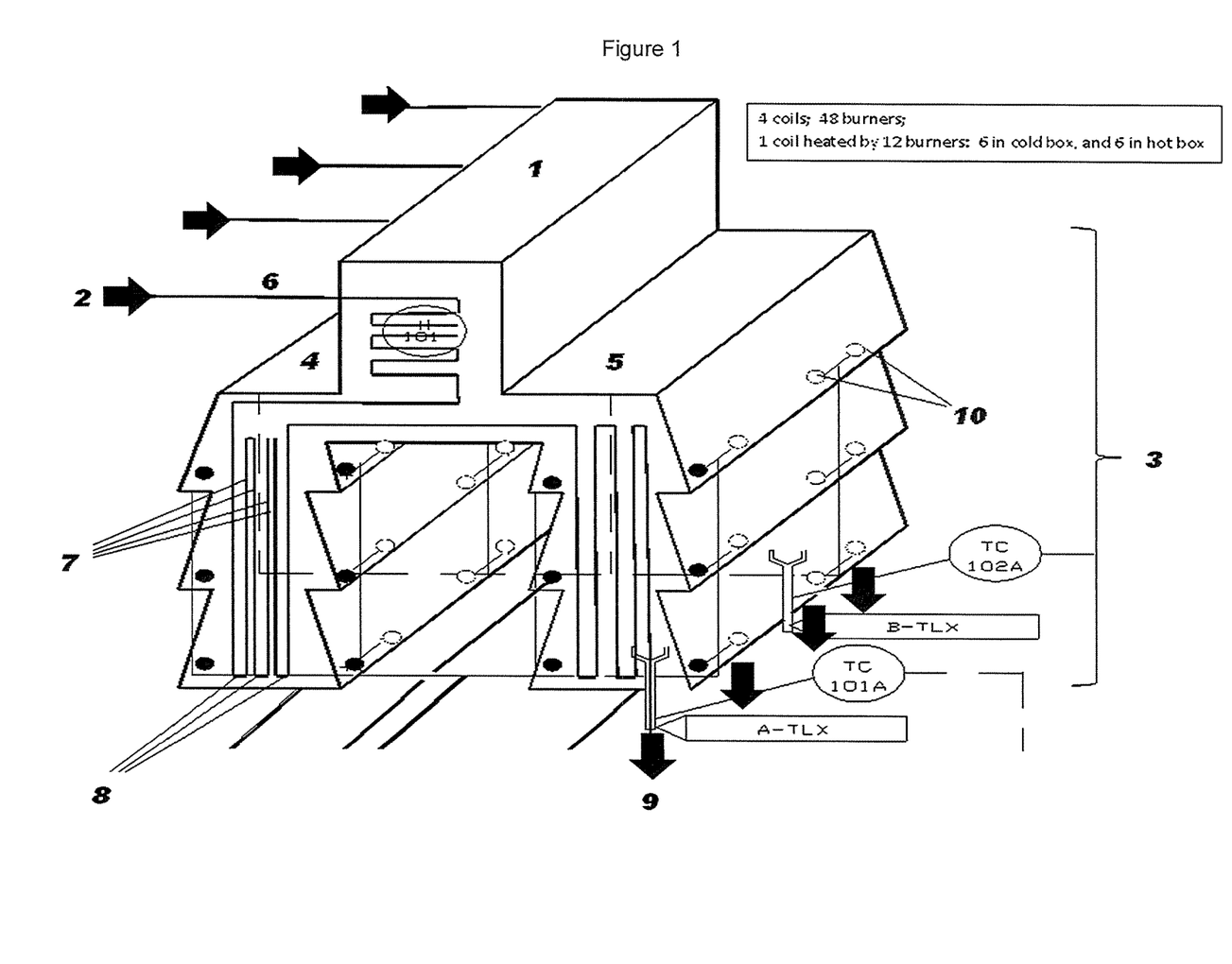
FIG. 1 is a schematic drawing of a cracking furnace.
Figure 2:
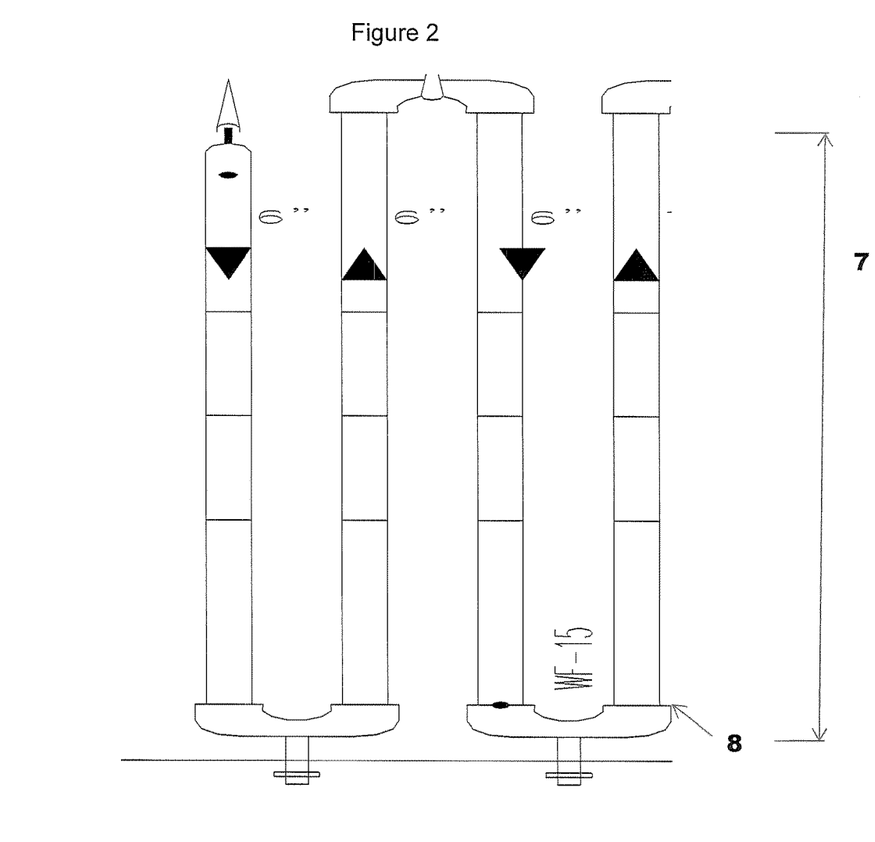
FIG. 2 is a schematic drawing of a part of a process coil.

In the manufacture of ethylene, a feed typically selected from the group consisting of $C_{2-4}$ alkanes, and naphtha is fed into one or more furnace coils which pass through a cracking furnace. The furnace, schematically shown in FIG. 1, includes two main parts: the convection section (1) where the feed (2) is initially preheated, and the radiant section (3) where the actual cracking process takes place. The radiant section of the furnace comprises the inlet (4), located downstream of the convection section which accounts for about half of the furnace radiant section and is sometimes referred to as a "cold" box, and the outlet (5) referred to as "hot" box. The feed flows through the process coil (6) which includes a long tube (7), suspended inside the inlet (4) and outlet (5) radiant sections of the furnace. To increase the length of the coil and, thus, to allow for the adequate residence time of the feed inside both radiant parts of the furnace, the coil comprises multiple vertical straight tubes (7), referred to as "passes", inter-connected with U-shaped elbows (8), as shown in FIG. 2. As the feed flows through the coil passes in the inlet radiant furnace section (4), ("cold" box), it is heated approximately to the temperature at which cracking reactions begin. Next, the feed leaves the inlet radiant section and flows through the passes of the process coils in the furnace outlet radiant section (5) ("hot" box,). In this section, the feed is further heated; the cracking reaction is progressing, until the final products (8) are extracted from the coil exit. In both parts of the furnace radiant section, the feed is heated by flames and by combustion gases generated by the burners (9) which are mounted on the furnace walls and on the furnace bottom. Heat transfer from combustion gases and flames to the processing coil (6) occurs predominantly by radiation and also, to a lesser extent, by the mechanism of forced convection. Flame and combustion gases heat not only the coils but also the furnace walls. The walls which are lined with a heat absorbing/radiating refractory, radiate heat on the coil, thus contributing to heating process of the flowing feed (2) as well.

If the efficiency of the heat transfer to the process coil in a furnace radiant section is maximized or just increased, fuel consumption by the burners can be reduced and, consequently, so are greenhouse gas emissions reduced. The increased efficiency of heat transfer in the radiant section provides also another possibility: the fuel consumption can be kept unchanged, but furnace capacity can be increased, i.e. higher feed flow rates can be cracked in the coil.

In accordance with the present invention one or more longitudinal vertical fins are added to the external surface of the process coil, at least to a portion of one or more passes (7), in the cracking furnace radiant section.

Figure 3:
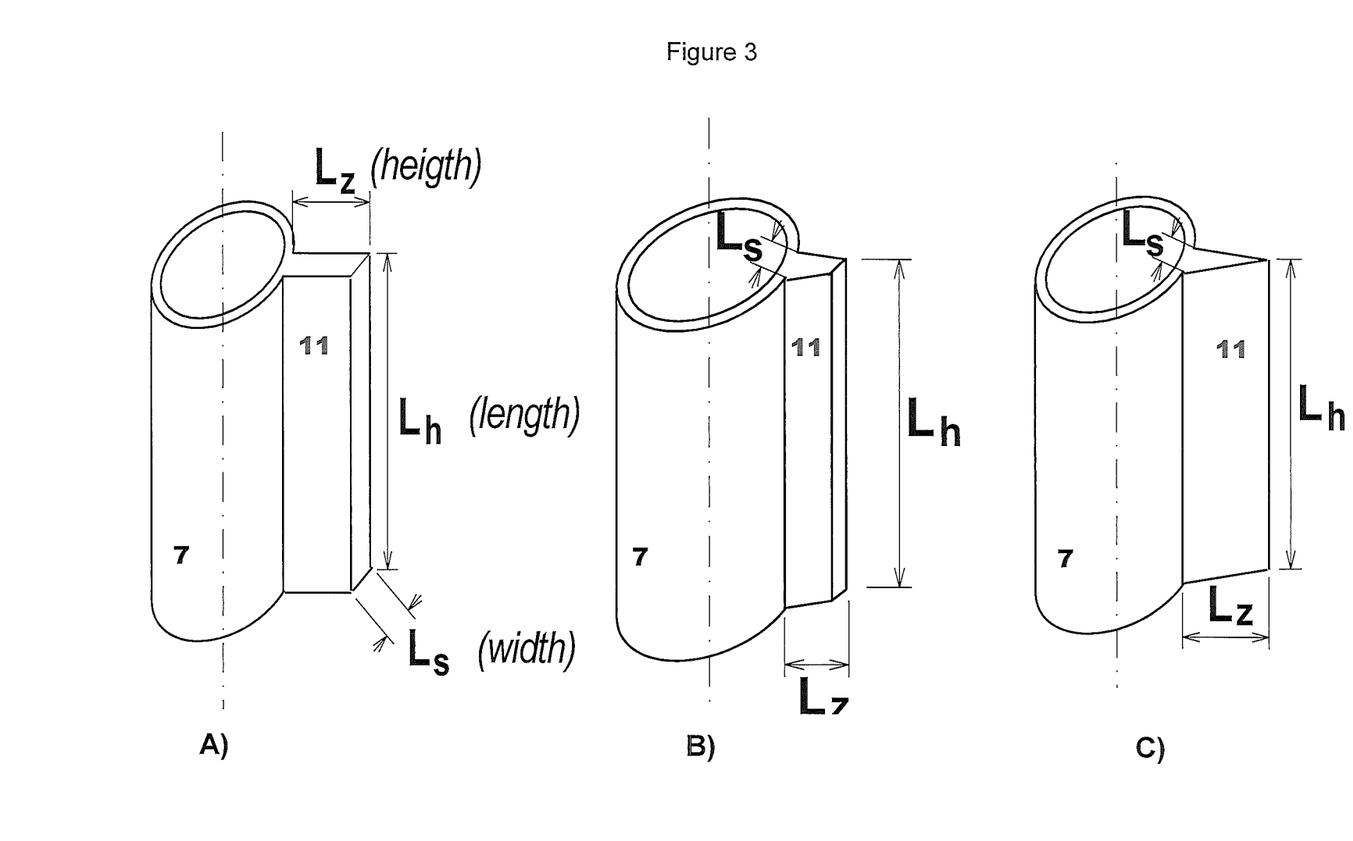
FIG. 3 is a schematic drawing of a geometry of longitudinal vertical fins, with: A) rectangular, B) triangular and C) trapezoidal cross sections, respectively, on a coil.

Typically, there could be from 1 to 8, preferably from 1 to 4, more preferably 1 or 2 longitudinal vertical fins (10), shown in FIG. 3, on the external surface of at least a portion of the coil single pass or, preferably, on more than one coil passes. If more than one fin is present, the fins may be radially evenly spaced about the outer circumference of the coil pass (e.g. two fins spaced 180° or four fins spaced 90° apart on the outer circumference of the coil pass). However, the fins spacing could be asymmetric. For example, for two fins the spacing could be from 160° to 200° radially apart on the external circumference of the radiant coil and two fins could be spaced from 60° to 120° radially apart.

The fin(s) (11), schematically shown in FIG. 3 are longitudinal vertical fins. The longitudinal vertical fins may have a number of cross sectional shapes, such as rectangular, square, triangular or trapezoidal as shown in part A, B and C of FIG. 3. A trapezoidal shape may not be entirely intentional, but may arise from the manufacturing process, for example when it is too difficult or costly to manufacture (e.g. cast or machine) a triangular cross section.

The fins can extend from 10% to 100% (and all ranges in between) of the length of the coil pass (7). However, the length ($L_h$) of the fin and location of the fin need not be uniform along all of the coil passes. In some embodiments of the invention, the fin could extend from 15 to 100%, typically from 30% to 100%, generally from 50% to 100% of the length of the pass of the radiant coil and be located at the bottom, middle or top of the pass (7). In further embodiments of the invention the fin could extend from 15% to 95%, preferably from 25% to 85% of the length of the coil pass (7) and be located centrally along the coil or be off set to the top or the bottom of the pass (7).

A fin may have at its base at the external circumference of the radiant coil, a width ($L_s$) from 3% to 30% of the coil outer diameter, typically from about 6% to 25%, preferably from 7% to 20%, most preferably from 7.5% to 15% of the coil outer diameter.

A fin may have a height ($L_z$) above the surface of the radiant coil from 10% to 50% of the coil outer diameter and all the ranges in between, preferably from 10% to 40%, typically from 10% to 35% of the coil outer diameter. The fins placed along coil passes may not have identical sizes in all locations in the radiant section, as the size of the fin may be selected based on the radiation flux at the location of the coil pass (7) (e.g. some locations may have a higher flux than others—corners).

In designing the fin care must be taken so that the fin adsorbs more radiant energy than it may radiate. This may be restated as the heat being transferred from the fin into the coil (through the base of the fin on the external surface of the coil) must be larger than the heat transferred through the same area on the surface of the bare finless coil. If the fin becomes too big (too high or too wide) the fin may start to reduce heat transfer, due to thermal effects of excessive conductive resistance (e.g. the fin radiates and gives away more heat than it absorbs), which defeats the purpose of the invention. Under the conditions of operation/use the transfer of heat through the base of the fin into the coil must exceed that transferred to the equivalent surface on a bare finless coil at the same conditions.

A coil pass may have a length from about 1.5 to 8 m, typically furnace tubes will have an outside diameter from 2 to 7 inches (e.g. 2 inch, 3 inch, 3.5 inch, 6 inch and 7 inch outside diameter) (about 3.7 to 20; typically about 5 to 16.5 cm (e.g. about 5 cm, about 7.6 cm, about 8.9 cm, about 15.2 cm and about 20 cm)) in outside diameter.

The fin(s) may comprise from 3% to 45%, preferably from 5% to 30% of the weight of the coil pass (7). One of the issues to consider is the creep of the coil pass (7) given the additional weight of the fins. Therefore, preferably, the fin(s) is an integral part of the coil pass and may be formed by casting the tube and/or machining a cast tube. As a result, preferably, the fin material has the same composition as the material of the pass (7) of the radiant coil.

The pass of the coil may be a tube of a stainless steel which may be selected from the group consisting of wrought stainless, austentic stainless steel and HP, HT, HU, HW and HX stainless steel, heat resistant steel, and nickel based alloys. The coil pass may be a high strength low alloy steel (HSLA); high strength structural steel or ultra high strength steel. The classification and composition of such steels are known to those skilled in the art.

In one embodiment the stainless steel, preferably heat resistant stainless steel typically comprises from 13 to 50, preferably 20 to 50, most preferably from 20 to 38 weight % of chromium. The stainless steel may further comprise from 20 to 50, preferably from 25 to 50 most preferably from 25 to 48, desirably from about 30 to 45 weight % of Ni. The balance of the stainless steel may be substantially iron.

The present invention may also be used with nickel and/or cobalt based extreme austentic high temperature alloys (HTAs). Typically the alloys comprise a major amount of nickel or cobalt. Typically the high temperature nickel based alloys comprise from about 50 to 70, preferably from about 55 to 65 weight % of Ni; from about 20 to 10 weight % of Cr; from about 20 to 10 weight % of Co; and from about 5 to 9 weight % of Fe and the balance one or more of the trace elements noted below to bring the composition up to 100 weight %. Typically the high temperature cobalt based alloys comprise from 40 to 65 weight % of Co; from 15 to 20 weight % of Cr; from 20 to 13 weight % of Ni; less than 4 weight % of Fe and the balance one or more trace elements as set out below and up to 20 weight % of W. The sum of the components adding up to 100 weight %.

Newer alloys may be used which contain up to about 12% Al, typically less than 7 weight %, generally about 2.5 to 3 weight % aluminum as disclosed for example in U.S. Pat. No. 7,278,828 issued Oct. 9, 2007 to Steplewski et al., assigned to General Electric Company. Typically in the high cobalt and high nickel steels the aluminum may be present in an amount up to 3 weight %, typically between 2.5 and 3 weight %. In the high chrome high nickel alloys (e.g. 13 to 50, preferably 20 to 50, weight % of Cr and from 20 to 50 weight % of Ni) the aluminum content may range up to 10, preferably less than about 7, typically from about 2 to 7 weight %.

In some embodiments of the invention the steel may further comprise a number of trace elements including at least 0.2 weight %, up to 3 weight % typically 1.0 weight %, up to 2.5 weight % preferably not more than 2 weight % of manganese; from 0.3 to 2, preferably 0.8 to 1.6 typically less than 1.9 weight % of Si; less than 3, typically less than 2 weight % of titanium, niobium (typically less than 2.0, preferably less than 1.5 weight % of niobium) and all other trace metals; and carbon in an amount of less than 2.0 weight %. The trace elements are present in amounts so that the composition of the steel totals 100 weight %.

The present invention will now be illustrated by the following non limiting examples.

EXAMPLES

Example 1

Validation of the Model of the Radiant Section of the Cracking Furnace

Figure 4:
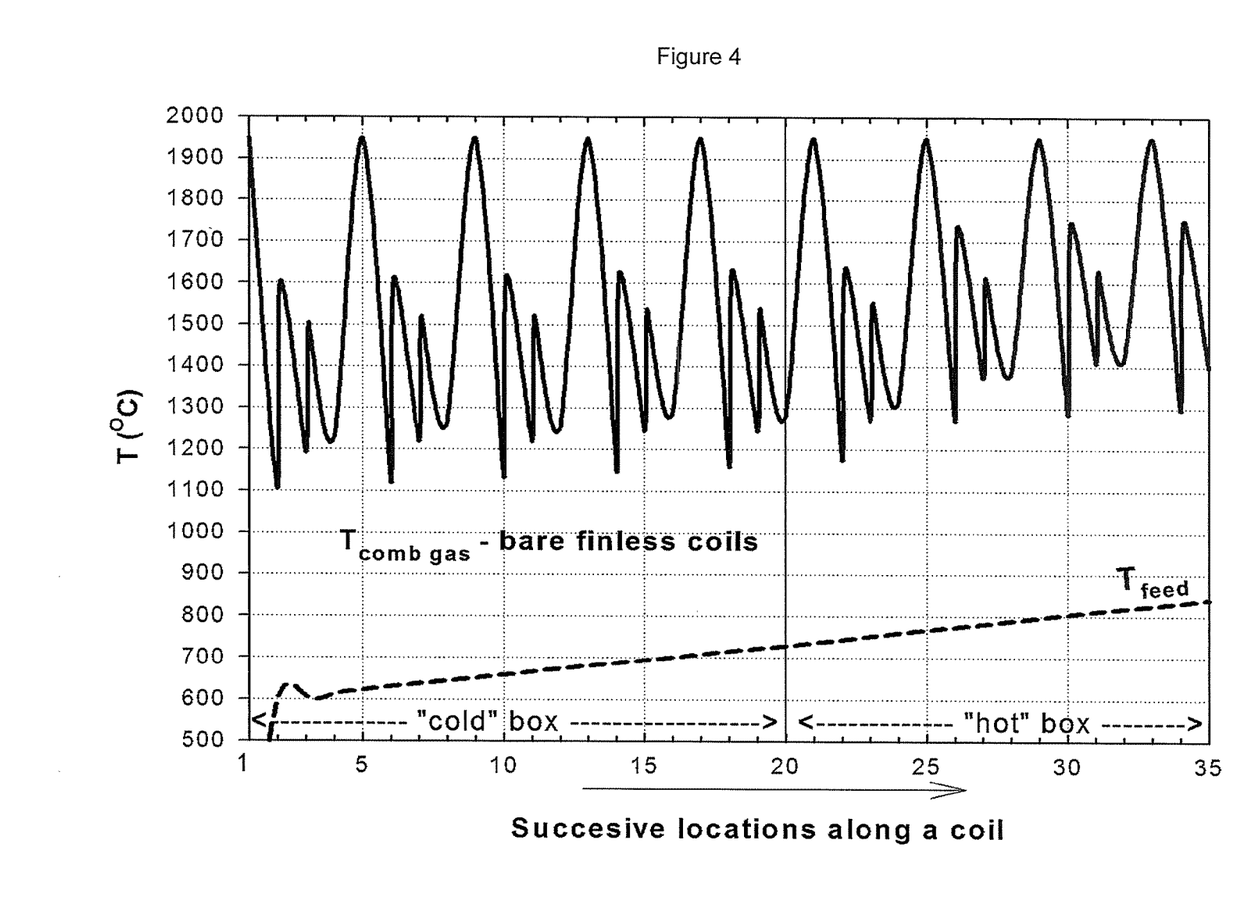
FIG. 4 is a plot of the calculated temperature distribution of combustion gases and feed, along the bare finless coils in a radiant furnace section, based on the computer simulation results of example 1.
Figure 5:
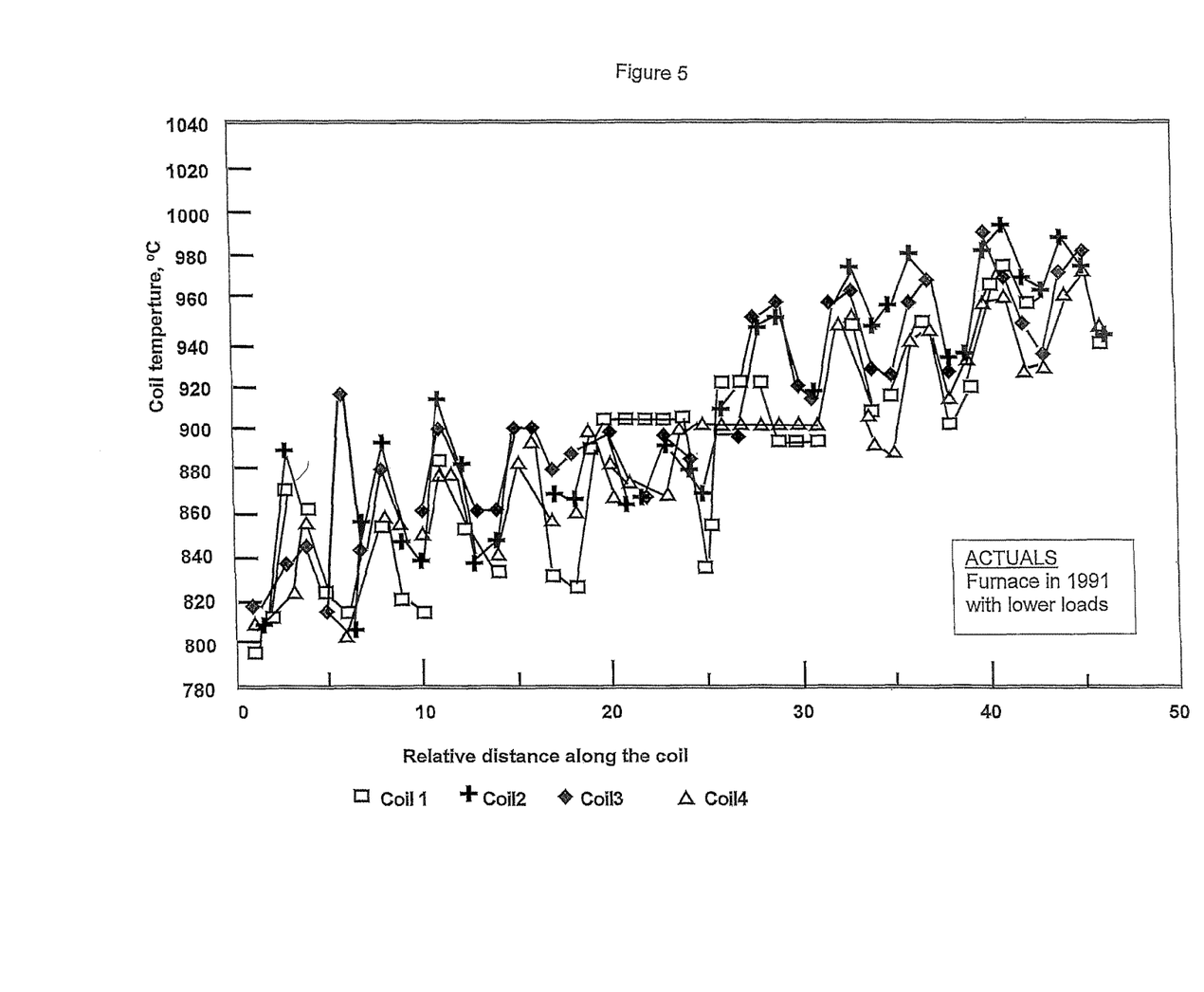
FIG. 5 is the actual temperature profile of the external surface of bare finless coils, measured in the radiant section of the cracking furnace that was operated with the similar parameters as used in the simulation in example 1.

A computer model of the radiant section of the NOVA Chemicals ethane cracker at Joffre was developed. The model was written using TK Solver (release 4) by Universal Technical System Inc. The model was run to simulate the process in the cracking furnace in which the coils in the furnace radiant section had no fins. The model predicted the temperature of the combustion gases, which flow along the process coils and transfer heat to the coil's external surface in the furnace radiant section. The results are shown in FIG. 4. The input data used for the above simulation, such as specific geometry and dimensions of the furnace and of the coils, feed flow rate, fuel gas composition and flow rate into the burners, feed and product compositions and temperatures at the inlet and outlet of the furnace radiant section, etc., were the actual operating data measured in a cracking furnace in Joffre. The calculated combustion gas temperatures were compared to the measured temperatures of the coil external surface, which are shown in FIG. 5. There was good qualitative agreement between the calculated combustion gas temperatures and the measured coil surface temperatures, so the model validly represents the operation of the furnace radiant section.

Example 2

Figure 6:
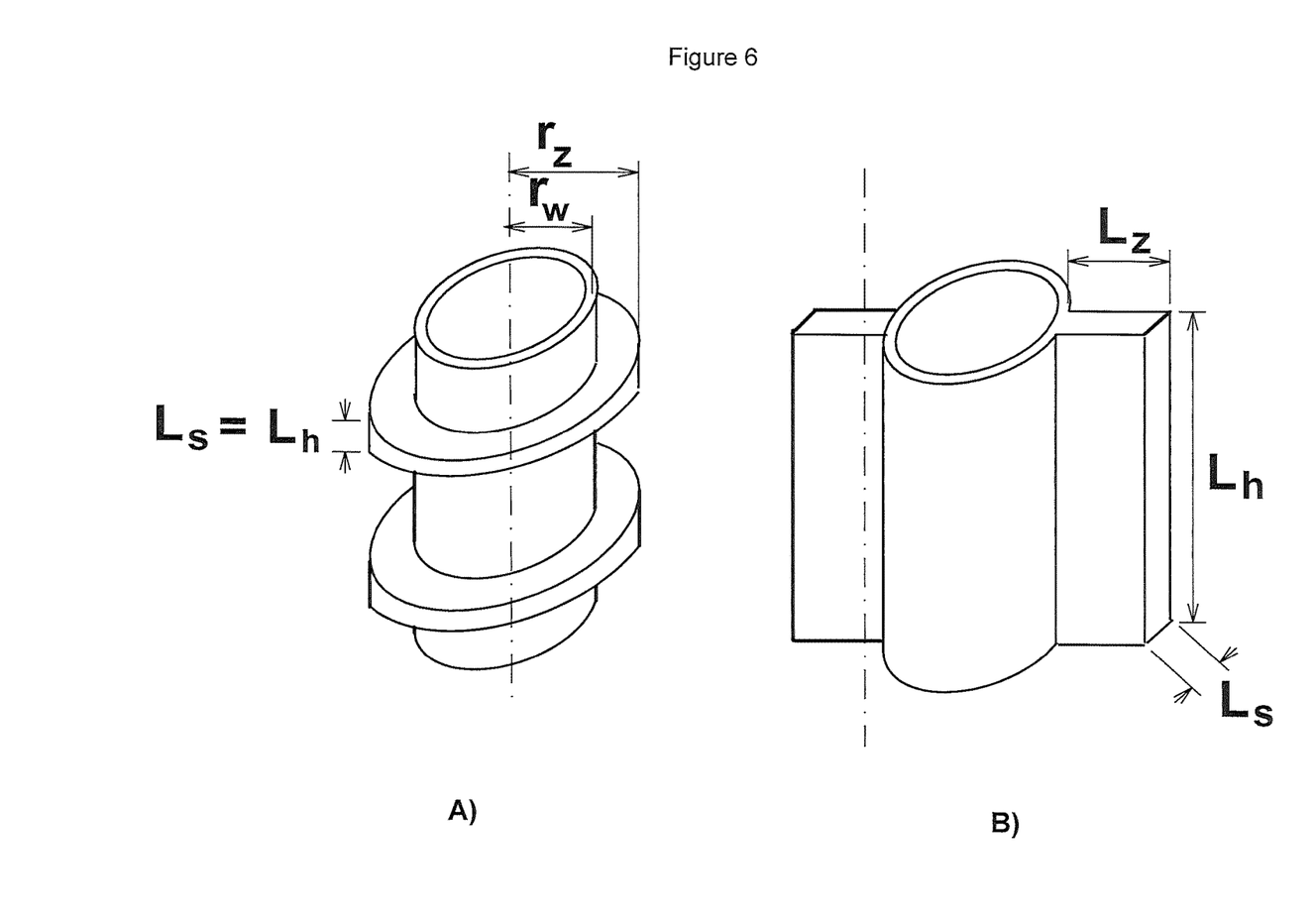
FIG. 6 shows the geometry of A) radial horizontal and B) longitudinal vertical fins, respectively, considered in the example 2.

Comparison of the fuel consumption and efficiency of a furnace which is equipped with:
  i) the bare radiant process coils (without fins);
  ii) the radiant coils having radial horizontal fins (per U.S. Pat. No. 7,128,139), shown in FIG. 6, part A); and
  iii) the radiant coils having two longitudinal vertical fins of the present invention, with a rectangular cross-section, as shown in FIG. 6, part B).

To have the basis for comparison between efficiency and performance of the radiant process coils representing the above three geometries, the following assumptions were made for the simulations purpose:

The total mass of the horizontal radial and longitudinal vertical fins was kept equal. This approach was taken because a significant limiting factor in coil design is mass of the fins. Increasing the fin dimensions and mass may improve the coil efficiency but it will also increase a coil tendency towards creep.

The dimensions of the bare radiant coils (diameter, wall thickness, length) were kept constant and identical for simulations of the above three geometries (i.e. finless bare coils and coils with fins) and they were equal to the actual dimensions of the finless coils, which are currently installed in Joffre cracking furnaces.

The radial horizontal coil fins, (FIG. 6, part A) had the radius of annular extension beyond the external surface of the coil of $r_z$=13.24 cm, and the width of the annulus of $L_h$=$L_s$ of 1 cm. The fins were distributed evenly along radiant coil passes in the furnace.

The longitudinal vertical coil fins, described in the present invention, comprised two fins of equal size, with the rectangular cross section and 180° apart on the pass sections of the furnace coil, FIG. 6, part B). Each fin had a length $L_h$ equivalent to the coil pass of 3 m, a height $L_z$ from the external surface of the coil of 5 cm and a width $L_s$ of 1 cm.

The following locations of the fins along the radiant coil were considered:
  (a) The radial horizontal fins and the longitudinal vertical fins were added to all coil passes in the furnace, in the inlet ("cold" box) and the outlet ("hot" box) furnace radiant sections;
  (b) The longitudinal vertical fins were added only to the coil passes in the outlet radiant section (in the "hot" box).

Figure 7:
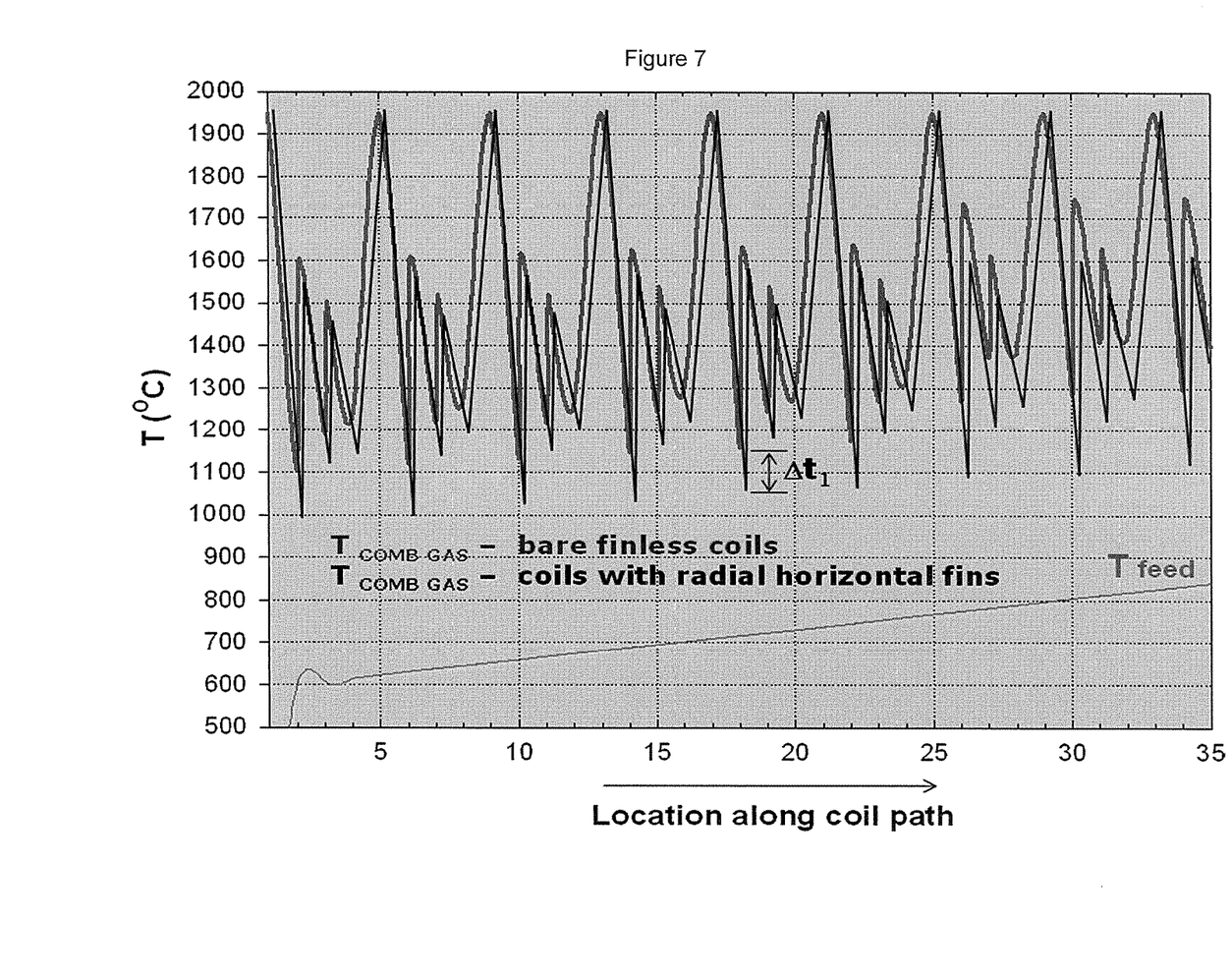
FIG. 7 is the graph comparing the calculated temperature distributions of combustion gases (and feed) along: (i) the bare finless process coils; and (ii) the coils with radial horizontal fins, in the furnace radiant section.
Figure 8:
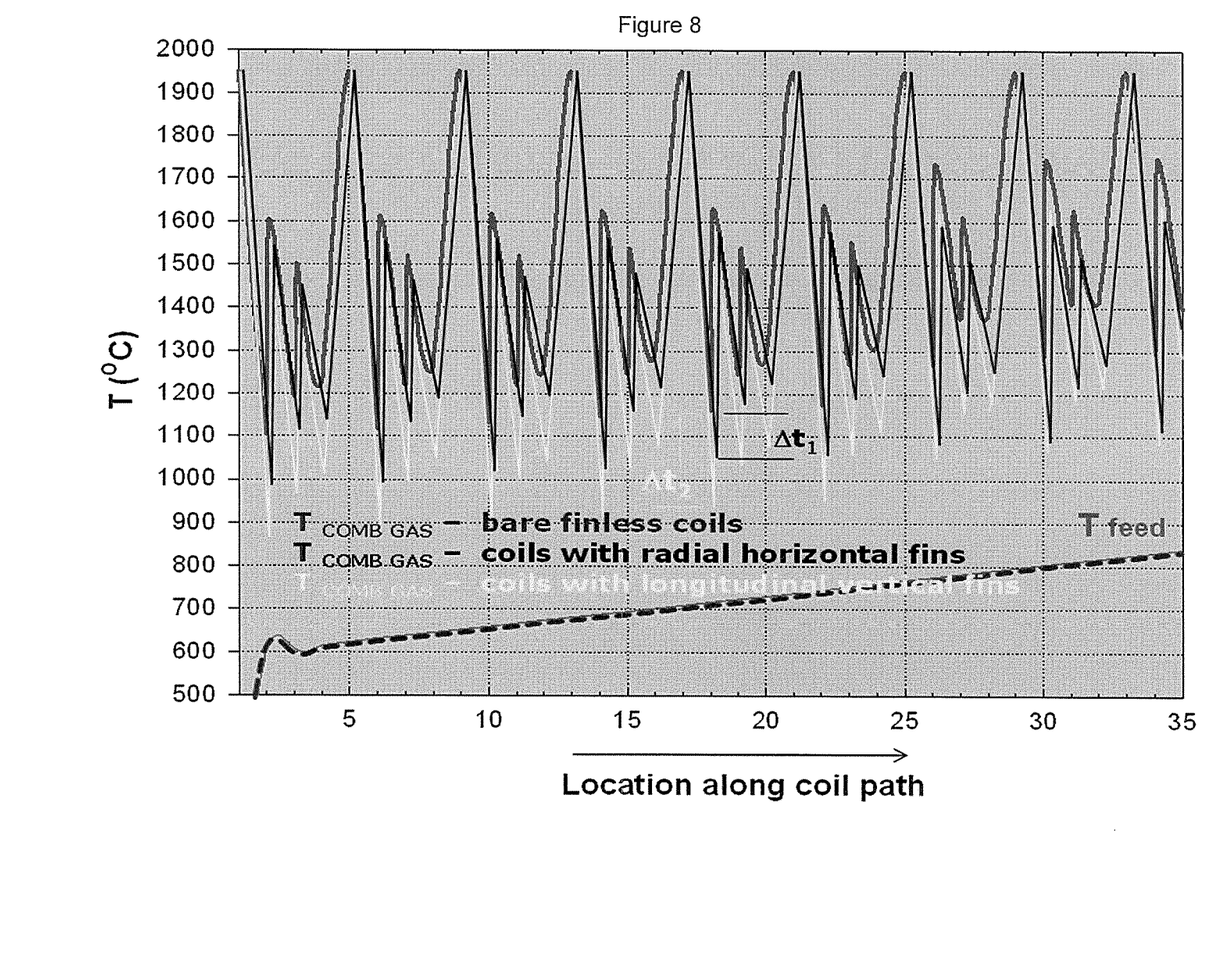
FIG. 8 is the graph showing the comparison of the calculated temperature distributions of combustion gases (and feed) along: (i) the bare finless process coils, (ii) the coils with radial horizontal fins; and (iii) the coils with longitudinal vertical fins, in the furnace radiant section.

The obtained simulation results are summarized in FIGS. 7 and 8.

The results shown in FIG. 7 indicate that addition of radial horizontal fins to the process coils improves heat transfer as compared to the case when process coils have no fin. The finned coils absorb more heat from combustion gases and as the result, the temperature of combustion gases flowing along coil path drops to lower levels, as compared to the case when process coils are finless. This more efficient "cooling" of combustion gases by coils with circular fins is represented in FIG. 7 by the temperature drop $\Delta t_1$.

The addition of the longitudinal vertical fins, improves heat transfer even more as shown in FIG. 8. The coils with vertical fins absorbs more heat from combustion gases than the coils with circular fins or bare finless coils and, as a result, the temperature of combustion gases flowing along coils with vertical fins drops to the lowest levels, represented in the FIG. 8 by the temperature drop $\Delta t_2$, ($\Delta t_2 > \Delta t_1$).

More effective heat absorption by finned coils allows to reduce fuel supply to the furnace and to increase efficiency of the furnace radiant section. The simulation results which quantify these changes are set forth in Table 1.

TABLE 1

Effect of addition of radial horizontal and longitudinal vertical fins to the process coils in a cracking furnace on fuel consumption and on efficiency of furnace radiant section

| Operational Parameters | Bare coils in the radiant furnace section ("cold" and "hot" boxes; Reference - the actual furnace) | Coils with radial horizontal fins in the radiant furnace section ("cold" and "hot" boxes) | Coils with 2 longitudinal vertical fins (with rectangular cross section) | |
|---|---|---|---|---|
| | | | in the radiant furnace section ("cold" and "hot" boxes) | in the second half of the radiant section ("hot" box) |
| Fin/coil mass ratio, % | 0 | 32.4 | 32.4 | 14.7 |
| Fuel supply to furnace burners, kg/s | 1.0 | 0.92 | 0.80 | 0.88 |
| Efficiency of furnace radiant section, % | 53.7 | 58.6 | 67.5 | 61.4 |

The above results demonstrate that the longitudinal vertical fins with rectangular cross section, added to the all coil passes in the radiant furnace section or added only to the coil passes in the second half of the radiant section (in the "hot" box) improve furnace efficiency above that of the furnace with the bare coils and above that of the furnace with the circular horizontal fins of U.S. Pat. No. 7,128,139, which have been added to all coil passes in the whole radiant furnace section (in "cold" and in "hot" boxes).

Based on the above comparison, it can be concluded that the further focus should be solely on the optimization of the longitudinal vertical fin as it significantly outperforms a horizontal circular fin for this particular application in the cracking furnace.

The next example is a step towards this optimization, as it evaluates efficiency of the longitudinal vertical fin with a triangular cross-section and compares it with the previously simulated longitudinal vertical fin with rectangular cross section.

Example 3

The example considers longitudinal vertical fin, with a triangular cross section, evaluates its effect on heat transfer and compares its performance with the vertical fin with the rectangular cross section that was previously analyzed in Example 2.

However, to simplify the comparison, instead of simulating the heat transfer in the entire furnace radiant section, with coils equipped with both types of fins, the comparison is made using the known analytical formulae for heat transferred through a single longitudinal vertical fin, with triangular and with the rectangular cross sections, respectively. Both types of fins, which have been previously shown in FIG. 3 part B and FIG. 3 part A, are assumed to be made of the same material, have the same length equal to a single coil pass (3 m) and be exposed to the same environment (i.e. to the same surrounding gas temperature and to the same convective and radiative heat transfer coefficients between gases and a fin). Heat transferred through each considered fin was estimated as follows:

Heat transferred through a single longitudinal vertical fin, with triangular cross section is:

$$Q_t = L_h \sqrt{2\alpha\lambda L_s} \, \Delta t \frac{I_1(c_1)}{I_0(c_1)}$$

-continued $$c_1 \equiv 2\sqrt{\frac{2\alpha L_z^2}{\lambda L_s}}$$

wherein
$Q_t$—total heat exchanged by a longitudinal vertical fin with a triangular cross section (kW);
$\lambda$—thermal conductivity of a fin (0.0303 kW/(m K));
$\alpha$—convective heat transfer coefficient. from hot gas to fin wall (~0.3 kW/(m² K));
$L_h$—fin length (m);
$L_s$—fin width (m);
$L_z$—fin height (m);
$\Delta t$—temperature difference between surrounding hot gas (~1600° C.) and temperature of the outer wall of a finned tube (~1000° C.);
$I_0$, $I_1$—Bessel functions of 0- and 1-order.

After such a fin is added to a process coil pass, the total heat transferred to the coil, $Q_{TOTAL}$, is the sum of the heat transferred through the fin-coil contact surface $Q'=Q_t$ and the heat transferred through the bare surface of a coil $Q''$.

$$Q_{TOTAL}=Q'+Q'''$$

Obviously, if the fin is effective, the percentage growth X of heat transferred to the finned coil will be larger than heat transferred to a finless coil, i.e. X>1.

Figure 9:
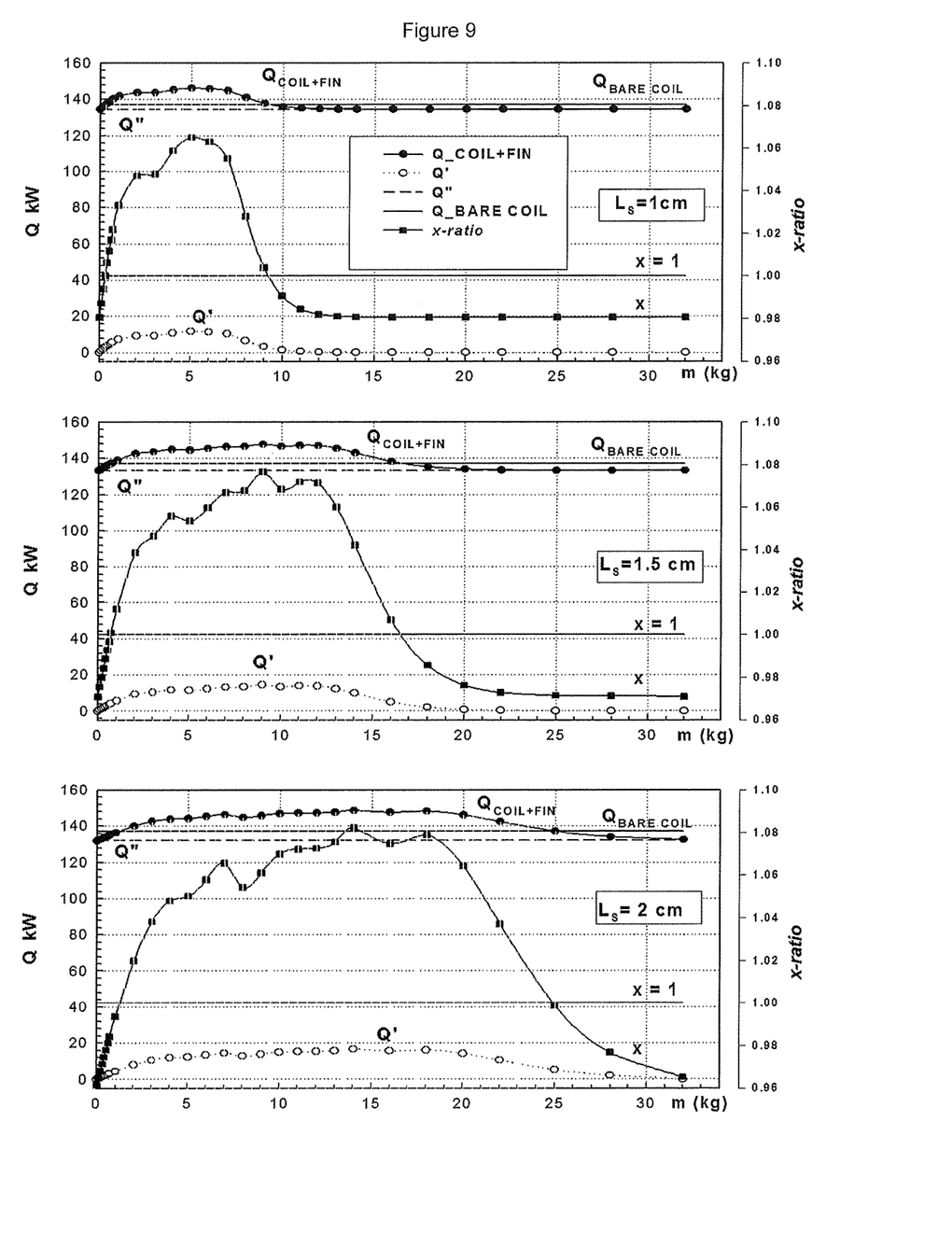
FIG. 9 shows heat transferred to a coil/tube with a single longitudinal vertical fin with triangular cross section, with a fixed length but with different mass and dimensions. The "efficient" range of the fin dimensions, which ensures that the fin increases heat transfer above the level transferred to a bare finless coil, is shaded on the graph.

A series of calculations were made to evaluate the performance of such triangular fins with different dimensions, which were added to a process coil, pass of a length of 3 meters. The results are presented in FIG. 9, for three triangular fins with different width at the fin base, $L_s$=1, 1.5 and 2 cm.

The results indicate that for a longitudinal vertical fin with triangular cross section, to be effective, the fin geometry represented by the height $L_z$, and thickness $L_s$, must be within the range which ensures that X>1. The range corresponds to the shaded areas in the FIG. 9.

For comparison purpose, the analogous values were calculated for a single longitudinal vertical fin with a rectangular cross section, using the following equation:

$$Q_r = \sqrt{\alpha O \lambda L_s L_h} \, \Delta t \frac{\sinh BL_z + \frac{\alpha}{B\lambda}\cosh BL_z}{\cosh BL_z + \frac{\alpha}{B\lambda}\sinh BL_z}$$

wherein:
   $Q_r$—total heat exchanged/transferred by a longitudinal vertical fin with a rectangular cross section (kW);
   λ—thermal conductivity of a fin (0.0303 kW/(m K);
   α—convective heat transfer coefficient from hot gas to wall (~0.3 kW/(m² K);
   O—perimeter of fin cross section (m); $O=2(L_s+L_h)$ $$B = \sqrt{\frac{\alpha O}{\lambda A}}$$

$L_h$—fin length (m);
   $L_s$—fin width (m);
   $L_z$—fin height (m);
   A—fin cross section $(A=L_h L_z)$, (m²);
   Δt—temperature difference between surrounding hot gas (~1600° C.) and temperature of the outer wall of finned tube (~1000° C.).

Using the above data, the calculations were made to evaluate performance of such a rectangular fin, assuming different fin dimensions (height $L_z$ and width $L_s$).

Figure 10:
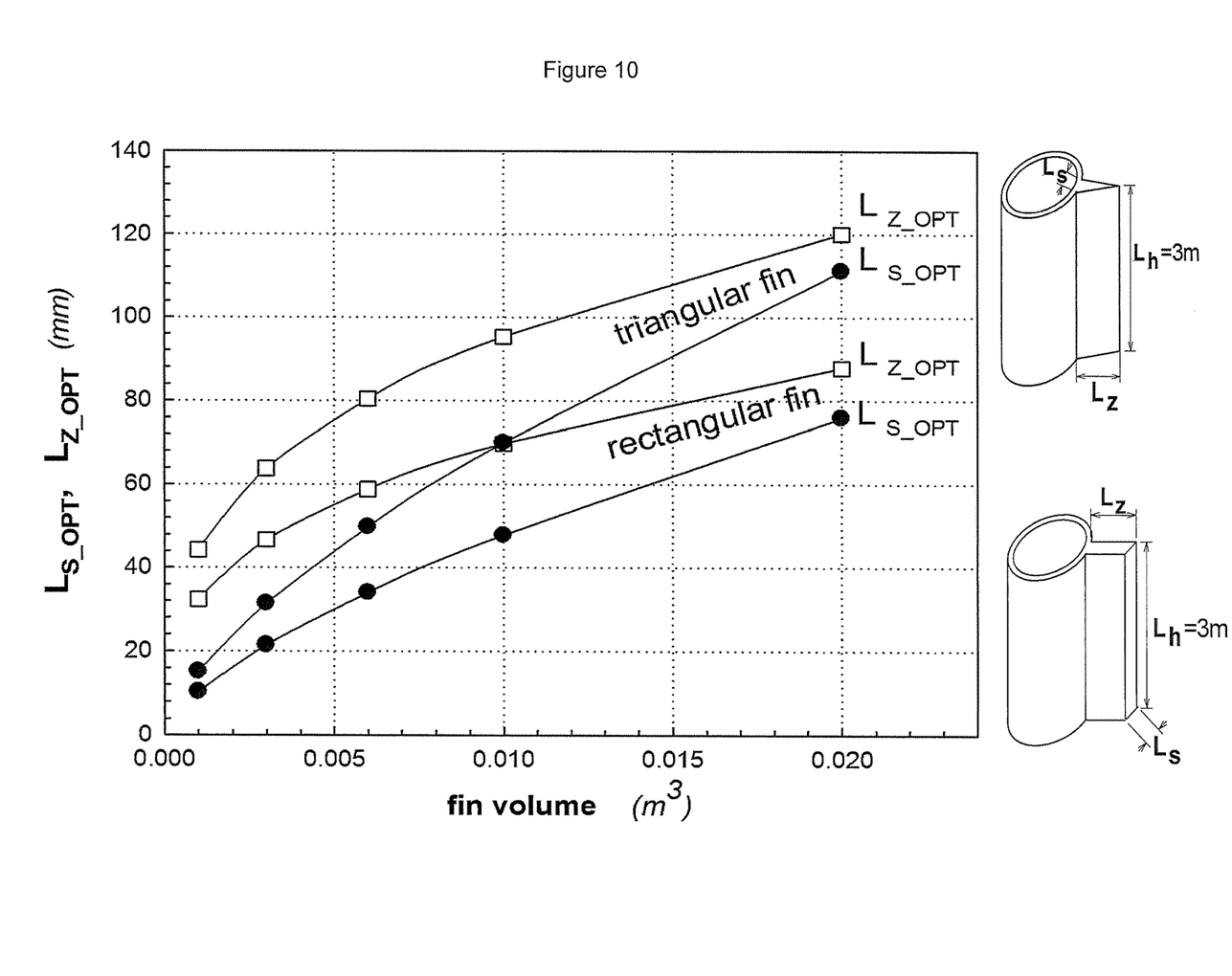
FIG. 10 is a comparison of volumes and dimensions for longitudinal vertical fins, with triangular and rectangular cross sections, for optimum heat transfer.

The results showing the optimum dimensions for both types of the longitudinal vertical fins, i.e. with a triangular and with rectangular cross sections, are summarized in FIG. 10 and performance evaluation for both types of fins is summarized in Table 2 below.

TABLE 2

Comparison of performance of a single longitudinal vertical fin with rectangular and with triangular cross sections

| Coil geometry | Dimensions, mm | | | Fin volume, cm³ | Fin mass, kg | Heat flux through the area on the coil surface, corresponding to the fin-coil contact surface | |
| --- | --- | --- | --- | --- | --- | --- | --- |
| | $L_h$ | $L_s$ | $L_z$ | | | kW | W/mm² |
| Bare coil | | | | | | | |
| No fins | 3000 | 10 | | 0 | 0 | | 9 |
| Coil with a single longitudinal vertical fin | | | | | | | |
| Fin cross section: rectangular | 3000 | 10 | 50 | 1500 | 11.8 | 19.96 | 39.92 |
| Fin cross section: triangular | 3000 | 10 | 50 | 750 | 5.89 | 17.78 | 35.56 |
| | 3000 | 10 | 100 | 1500 | 11.8 | 19.07 | 19.07 |
| | 3000 | 20 | 50 | 1500 | 11.8 | 23.47 | 23.47 |

The results indicate the following trends:
A properly designed longitudinal vertical fin with triangular cross section, can slightly outperform a longitudinal vertical fin with rectangular cross section, as it can deliver through its base more heat to a coil, (23.47 kW vs. 19.96 kW), while maintaining the same mass as the rectangular fin (11.8 kg);
Further, a fin should be generally designed as "stubby", with a relatively large contact (base) surface between the fin and the coil, and with a relatively small fin height.

What is claimed is:

1. In a furnace for thermally cracking a gaseous feed selected from the group consisting of $C_{2-4}$ alkanes and naphtha, fed to one or more process coils in the furnace radiant section having combustion gasses passing there through comprising one or more of floor and wall burners and having radiant refractory walls the improvement comprising using in said radiant section one or more process coils comprising one or more passes, having a circular cross section and from 1 to 8 substantially linear longitudinal vertical fins having cross section which is a trapezoid on the external surface, said fins having:
   (i) a length from 10 to 100% of the length of the coil pass;
   (ii) a base having a width from 3% to 30% of the coil outer diameter, which base has continuous contact with, or is integrally part of the coil pass;
   (iii) a height from 10% to 50% of the coil outer diameter;
   (iv) a weight from 3% to 45% of the total weight of the coil pass; and
   (v) adsorbing more radiant energy than they radiate.

2. The furnace according to claim 1, in which the number of fins is from one to four.

3. The furnace according to claim 2, in which each fin has a base from 4% to 20% of the coil outer diameter.

4. The furnace according to claim 3, in which each fin has a height from 13% to 35% of the coil outer diameter.

5. The furnace according to claim 4, wherein each fin has a weight of not less than 5% of the weight of the coil pass.

6. The furnace according to claim 5, wherein the one or more furnace radiant coils comprise from about 55 to 65 weight % of Ni; from about 20 to 10 weight % of Cr; from about 20 to 10 weight % of Co; and from about 5 to 9 weight % of Fe and the balance one or more of the trace elements.

7. The furnace according to claim 6, wherein the trace elements comprise from 0.2 up to 3 weight % of Mn; from 0.3 to 2 weight % of Si; less than 5 weight % of titanium, niobium and all other trace metals; and carbon in an amount of less than 0.75 weight % the sum of the components adding up to 100 weight %.

8. The furnace according to claim 7, wherein the one or more furnace radiant coils further comprise from 2.5 to 3 weight % aluminum.

9. The furnace according to claim 5, wherein the one or more furnace radiant coils comprise from 40 to 65 weight % of Co; from 15 to 20 weight % of Cr; from 20 to 13 weight % of Ni; less than 4 weight % of Fe and the balance of one or more trace elements and up to 20 weight % of W the sum of the components adding up to 100 weight %.

10. The furnace according to claim 9, wherein the trace elements comprise from 0.2 up to 3 weight % of Mn; from 0.3 to 2 weight % of Si; less than 5 weight % of titanium, niobium and all other trace metals; and carbon in an amount of less than 0.75 weight %.

11. The furnace according to claim 10, wherein the one or more furnace radiant coils further comprise from 2.5 to 3 weight % aluminum.

12. The furnace according to claim 5, wherein the one or more furnace radiant coils comprise from 20 to 38 weight % of chromium from 25 to 48, weight % of Ni.

13. The furnace according to claim 12, wherein the one or more furnace radiant coils further comprise from 0.2 up to 3 weight % of Mn, from 0.3 to 2 weight % of Si; less than 5 weight % of titanium, niobium and all other trace metals; and carbon in an amount of less than 0.75 weight % and the balance substantially iron.

14. The furnace according to claim 13, wherein the one or more furnace radiant coils further comprise from 2 to 7 weight % aluminum.

15. The furnace according to claim 6, wherein there are two fins on the one or more furnace coils radially spaced from 160° to 200° from each other about the external surface of the furnace coil.

16. The furnace according to claim 9, wherein there are two fins on the one or more furnace coils, radially spaced from 160° to 200° from each other about the external surface of the one or more furnace coils.

17. The furnace according to claim 12, wherein there are two fins on the one or more furnace coils radially spaced from 160° to 200° from each other about the external surface of the one or more furnace coils.

18. The furnace according to claim 15, wherein only that portion of the one or more furnace coils passes in the radiant section have fins.

19. The furnace according to claim 16, wherein only that portion of the one or more furnace coils passes in the radiant section have fins.

20. The furnace according to claim 17, wherein only that portion of the one or more furnace coils passes in the radiant section have fins.

* * * * *